(12) United States Patent
Ebetino et al.

(10) Patent No.: US 8,252,774 B2
(45) Date of Patent: Aug. 28, 2012

(54) 5-AZAINDOLE BISPHOSPHONATES

(75) Inventors: Frank Hallock Ebetino, Cincinnati, OH (US); Adam Mazur, Cincinnati, OH (US); Mark Walden Lundy, Cincinnati, OH (US); Robert Graham Russell, Oxford (GB)

(73) Assignee: Isis Innovation Ltd., Oxford (GB)

( * ) Notice: Subject to any disclaimer, the term of this patent is extended or adjusted under 35 U.S.C. 154(b) by 0 days.

(21) Appl. No.: 13/120,090

(22) PCT Filed: Sep. 22, 2009

(86) PCT No.: PCT/US2009/057821
§ 371 (c)(1),
(2), (4) Date: Jun. 10, 2011

(87) PCT Pub. No.: WO2010/033981
PCT Pub. Date: Mar. 25, 2010

(65) Prior Publication Data
US 2011/0237550 A1 Sep. 29, 2011

Related U.S. Application Data

(60) Provisional application No. 61/099,082, filed on Sep. 22, 2008.

(51) Int. Cl.
*A61K 31/663* (2006.01)
*C07F 9/02* (2006.01)
(52) U.S. Cl. .............................. 514/81; 546/23
(58) Field of Classification Search .................. 514/81; 546/23
See application file for complete search history.

(56) References Cited

U.S. PATENT DOCUMENTS

| 3,992,392 A | 11/1976 | Gassman |
| 6,686,374 B1 | 2/2004 | Edwards et al. |
| 7,169,787 B2 | 1/2007 | Hofgen et al. |
| 2004/0224971 A1 | 11/2004 | Hofgen et al. |

OTHER PUBLICATIONS

PCT International Search Report dated May 10, 2010.

*Primary Examiner* — Rebecca Anderson
*Assistant Examiner* — Samantha Shterengarts
(74) *Attorney, Agent, or Firm* — Thomas, Kayden, Horstemeyer & Risley, LLP

(57) ABSTRACT

Novel 5-azaindole bisphosphonate compounds are disclosed, as well as methods of preparing the compounds, pharmaceutical compositions including the compounds, and administration of the compounds in methods of treating abnormal calcium and phosphate metabolism, including bone and joint diseases and other disorders.

16 Claims, 2 Drawing Sheets

2

3

6

I

5-AZAINDOLE BISPHOSPHONATES

CROSS-REFERENCE TO RELATED APPLICATIONS

This application is the National Stage of International Application No. PCT/US2009/057821 filed Sep. 22, 2009, which claims to the benefit of U.S. Provisional Patent Application Ser. No. 61/099,082, entitled "5-AZAINDOLE BISPHOSPHONATES" filed on Sep. 22, 2008, the contents of which are incorporated by reference as if fully set forth herein.

FIELD OF THE DISCLOSURE

Novel bisphosphonate compounds are disclosed, as well as their activity as anti-resorptive agents and for treatment and prevention of disorders associated with bone metabolism, abnormal calcium and phosphate metabolism, and other disorders. Processes for preparing the novel bisphosphonate compounds, as well as methods of using them and pharmaceutical compositions containing them are also disclosed

BACKGROUND

Bisphosphonates were first developed to complex calcium in hard water to improve detergent performance. Bisphosphonates have since been found to be useful in the treatment and prevention of diseases or conditions characterized by abnormal calcium and phosphate metabolism. Such conditions may be divided into two broad categories: conditions that are characterized by anomalous mobilization of calcium and phosphate leading to general or specific bone loss or excessively high calcium and phosphate levels in the fluids of the body. Such conditions are sometimes referred to as pathological hard tissue demineralization; and conditions which cause or result from deposition of calcium and phosphate anomalously in the body. These latter conditions are sometimes referred to as pathological calcifications.

The first category includes osteoporosis, a condition in which bone hard tissue is lost disproportionately to the development of new hard tissue ultimately resulting in fractures. Essential quantities of cancellous and cortical bone are lost, and marrow and bone spaces become larger, resulting in reduced bone strength. Bone also becomes less dense and fragile. Osteoporosis can be sub-classified as genetic, senile, drug-induced (e.g., adrenocorticoid, as can occur in steroid therapy), disease-induced (e.g., arthritic and tumor), etc., however the manifestations are similar. Another condition in the first category is Paget's disease (osteitis deformans). In this disease, dissolution of normal bone occurs, which is then haphazardly replaced by soft, poorly mineralized tissue such that the bone becomes deformed from pressures of weight bearing, particularly in the tibia and femur. Hyperparathyroidism, hypercalcemia of malignancy, and osteolytic bone metastasis are conditions also included in the first category.

The second category, involving conditions manifested by anomalous calcium and phosphate deposition, includes myositis ossificans progressiva, calcinosis universalis, and such afflictions as arthritis, neuritis, bursitis, tendonitis, and other inflammatory conditions which predispose involved tissue to deposition of calcium phosphates.

A variety of polyphosphonic acid derivatives have been proposed for use in the treatment and prophylaxis of conditions involving abnormal calcium and phosphate metabolism. For example diphosphonates, like ethane-1-hydroxy-1,1-diphosphonic acid (EHDP), propane-3-amino-1-hydroxy-1,1-diphosphonic acid (APD), and dichloromethane diphosphonic acid ($Cl_2MDP$) have been the subject of considerable research efforts in this area. Paget's disease and heterotopic ossification have been treated with EHDP. Similarly, risedronate and alendronate have been used for treatment of bone disorders, and U.S. Pat. No. 4,990,503 discloses heterocyclic bisphosphonic acid derivatives and their use as bone resorption inhibitors.

Bisphosphonates tend to inhibit the resorption of bone tissue, which is beneficial to patients suffering from excessive bone loss. However, many of the early bisphosphonates, such as EHDP, APD, and $Cl_2MDP$, have a greater propensity of inhibiting bone mineralization at high doses, a phenomenon which is particularly problematic during the course of long term treatment. Bone mineralization is essential for treatment of disorders such as osteoporosis. Bone tissue that is not adequately mineralized is soft and flexible and does not contribute to bone strength or skeletal support. Accordingly, long-term inhibition of mineralization could result in harmful side effects, such as increased risk of fracture, rickets in children and osteomalacia in adults. Even with the development of more potent bisphosphonates, which allows for administration of smaller dosages, there is still a potential for bone mineralization defects.

Farnesyl pyrophosphate synthase (FPPS) is a key regulatory enzyme in the mevalonate pathway. This pathway, ubiquitous in mammalian cells, provides essential lipid molecules, such as cholesterol and isoprenoids, with the latter necessary for posttranslational prenylation of small GTPases. The blockage of this pathway is a concept that has found widespread clinical use, with statins as drugs that inhibit hydroxymethylglutaryl CoA reductase and reduce cholesterol biosynthesis, and nitrogen-containing bisphosphonates (N-BPs) as drugs for osteoporosis therapy that target FPPS and inhibit protein prenylation. In the case of N-BPs, the unique bone-targeting pharmacokinetic properties of these compounds cause selected inhibition of FPPS and loss of prenylated proteins in osteoclasts, thereby inhibiting the bone-destroying function of these cells.

SUMMARY

The 5-azaindole bisphosphonate derivatives described herein are useful in the treatment and/or prevention of disorders associated with abnormal calcium and phosphate metabolism, including bone and joint disorders such as osteoporosis, rheumatoid arthritis, osteoarthritis, Paget's disease, alveolar bone loss often associated with periodontal disease and bone-related cancer therapy. The compounds described herein have the ability to inhibit the resorption of bone tissue and are inhibitors of farnesyl pyrophosphate synthase (FPPS). Furthermore, such compounds correspondingly have orthopedic uses (including, but not restricted to, fracture repair and implant fixation; and prevention of prosthesis loosening, and osteonecrosis of various bones). Other uses include immunomodulation and anti-inflammatory effects, and use in various parasitic disorders (eg. malaria, leishmaniasis, trypanasomal diseases, entamoeba, giardia, and cryptosporidial infections).

One aspect of the present disclosure, therefore, encompasses compounds, or pharmaceutically acceptable salts thereof, where the compound has a structure according to the general formula I

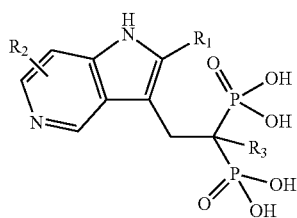

(I)

where $R_1$ is hydrogen, hydroxyl, lower alkyl, methoxy, or F; $R_2$ is hydrogen, hydroxyl, lower alkyl, or F; and $R_3$ is F, Cl, or hydrogen.

In embodiments of this aspect of the disclosure, $R_1$ and $R_2$ can be each independently hydrogen, hydroxyl, methyl, ethyl, t-butyl, or F.

In some embodiments of the disclosure, $R_1$ can be hydrogen or a lower alkyl, and $R_2$ can be hydrogen, hydroxyl, methyl, or F.

In other embodiments of this aspect of the disclosure, $R_1$ can be hydrogen, ethyl, or t-butyl, and $R_2$ can be hydrogen, hydroxyl, methyl, or F. In some embodiments, $R_3$ can be hydrogen or F.

In some embodiments of this aspect of the disclosure, $R_1$ can be hydrogen, $R_2$ can be hydrogen or methyl, and $R_3$ can be hydrogen or F.

In some other embodiments of this aspect of the disclosure, $R_1$ is ethyl or t-butyl, $R_2$ is hydrogen, and $R_3$ is hydrogen or F.

Embodiments of this aspect of the disclosure can be, but are not limited to, compounds wherein the compound has a structure according to Formula Ia:

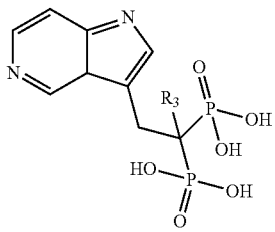

(Ia)

In one embodiment, thereof, $R_3$ is hydrogen and the compound is 5-azaindol-3-yl-ethyl-bisphosphonic acid. In another embodiment thereof, $R_3$ is F and the compound is 1-fluoro-(5-azaindol)-3-yl-ethyl-bisphosphonic acid.

Another aspect of the disclosure encompasses pharmaceutical compositions that comprise a compound, or a pharmaceutically acceptable salt thereof, wherein the compound has a structure according to Formula I

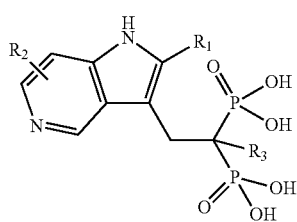

(I)

where $R_1$ is hydrogen, hydroxyl, lower alkyl, methoxy, or F; $R_2$ is hydrogen, hydroxyl, lower alkyl, or F; and $R_3$ is F, Cl, or hydrogen, and a pharmaceutically acceptable carrier.

In embodiments of this aspect of the disclosure, $R_1$ and $R_2$ can be each independently hydrogen, hydroxyl, methyl, ethyl, t-butyl, or F.

In some embodiments of the disclosure, $R_1$ can be hydrogen or a lower alkyl, and $R_2$ can be hydrogen, hydroxyl, methyl, or F.

In other embodiments of this aspect of the disclosure, $R_1$ can be hydrogen, ethyl, or t-butyl, and $R_2$ can be hydrogen, hydroxyl, methyl, or F. In some embodiments, $R_3$ can be hydrogen or F.

In some embodiments of this aspect of the disclosure, $R_1$ can be hydrogen, $R_2$ can be hydrogen or methyl, and $R_3$ can be hydrogen or F.

In some other embodiments of this aspect of the disclosure, $R_1$ is ethyl or t-butyl, $R_2$ is hydrogen, and $R_3$ is hydrogen or F.

In some embodiments of this aspect of the disclosure, the compound can have a structure according to Formula Ia:

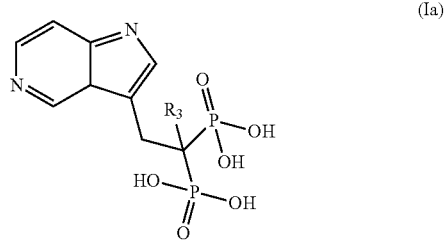

(Ia)

In one of these embodiments $R_3$ can be hydrogen and the compound is 5-azaindol-3-yl-ethyl-bisphosphonic acid. In another embodiment, $R_3$ is F and the compound is 1-fluoro-(5-azaindol)-3-yl-ethyl-bisphosphonic acid.

Yet another aspect of the disclosure encompasses methods of modulating calcium or phosphate metabolism in a subject animal or human, the method comprising administering to the subject animal or human an effective amount of a compound, or pharmaceutically acceptable salt thereof, where the compound has a structure according to Formula I

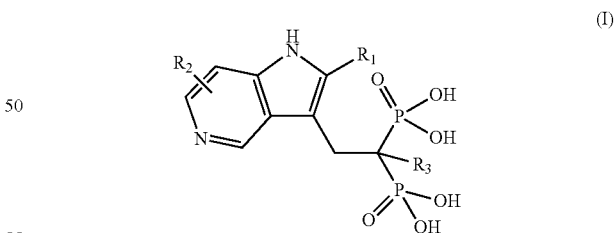

(I)

where $R_1$ is hydrogen, hydroxyl, lower alkyl, methoxy, or F; $R_2$ is hydrogen, hydroxyl, lower alkyl, or F; and $R_3$ is F, Cl, or hydrogen, whereupon the calcium or phosphate metabolism in the subject animal or human is modified.

In embodiments of the methods of this aspect of the disclosure, the calcium or phosphate metabolism in the subject animal or human before administering the compound thereto can be abnormal and associated with a skeletal disorder. In some embodiments of this aspect of the disclosure, the skeletal disorder can be selected from the group consisting of, but is not limited to, osteoporosis, rheumatoid arthritis, osteoarthritis, Paget's disease, alveolar bone loss, a bone-related cancer, and an orthopedic disorder.

In other embodiments, the disorder may be a non-skeletal disorder such as, but not limited to, a non-bone cancer, an immunomodulatory disorder, an inflammatory disorder, or a parasitic disorder. In these embodiments, the parasitic disorder can be, but is not limited to, malaria, leishmaniasis, a trypanasomal disease, an entamoebal infection, a giardia infection, and a cryptosporidial infection.

In the embodiments of the methods of this aspect of the disclosure, the compound administered to the subject animal or human can modify the activity of farnesyl pyrophosphate synthase in the subject animal or human.

In the embodiments of the methods of this aspect of the disclosure, the compound, or pharmaceutically acceptable salt thereof, or is 5-azaindol-3-yl-ethyl-bisphosphonic acid or 1-fluoro-(5-azaindol)-3-yl-ethyl-bisphosphonic acid.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
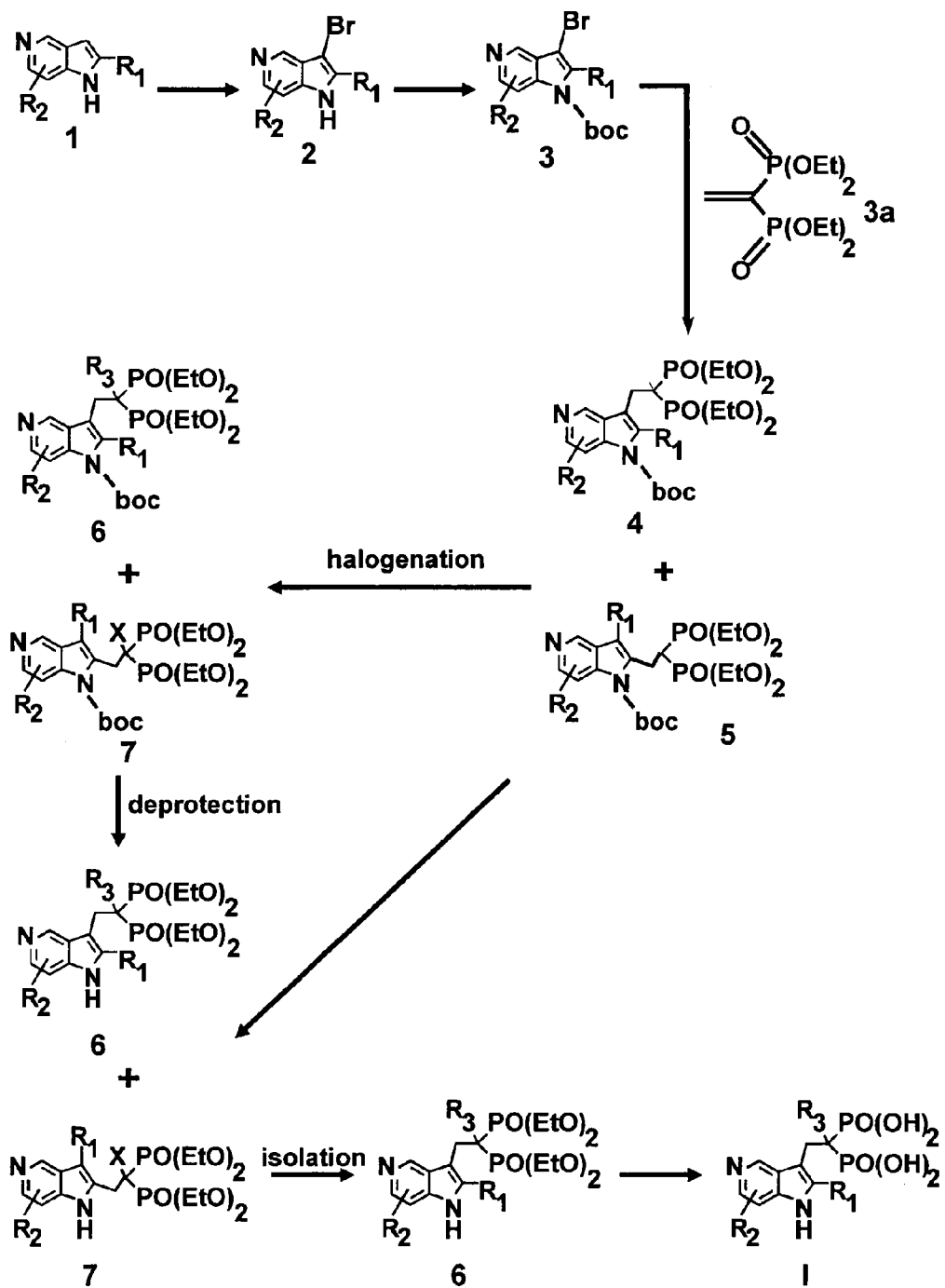
FIG. 1 schematically illustrates Scheme 1 as a process for making compounds of Formula I.
Figure 2:
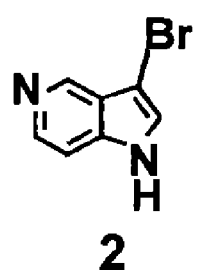
FIG. 2 schematically illustrates the structures of the products: 3-bromo-5-azaindole; N—BOC-3-bromo-5-azaindole; Tetraethyl-5-azaindol-3-yl-ethyl-bisphosphonate; 5-azaindol-3-yl-ethyl-bisphosphonic acid of the reactions described in Examples 1-4, respectively.
Figure 2:
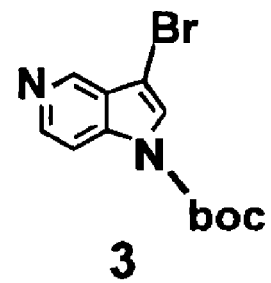
Figure 2:
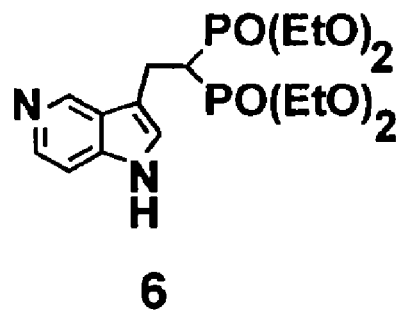
Figure 2:
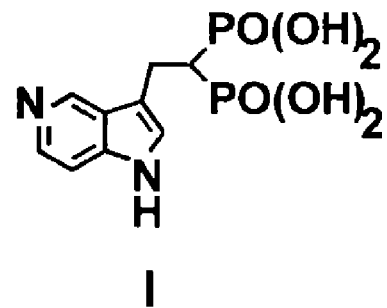

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Abbreviations

EHDP, ethane-1-hydroxy-1,1-diphosphonic acid; APD, propane-3-amino-1-hydroxy-1,1-diphosphonic acid; Cl$_2$MDP dichloromethane diphosphonic acid; FPPS, farnesyl pyrophosphate synthase; N-BP, nitrogen-containing bisphosphonate Definitions The term "lower alkyl" as used herein refers to a linear or branched, saturated hydrocarbon having from 1 to 4 carbon atoms. Representative (C$_1$-C$_4$)-alkyl groups include, but are not limited to, methyl, ethyl, propyl, isopropyl, butyl, sec-butyl, and tert-butyl. Similarly, "(C$_1$-C$_4$)-alkyl" as used herein refers to a linear or branched, saturated hydrocarbon, optionally substituted as described above, having from 1 to 4 carbon atoms. The carbon number, as used herein, refers to the carbon backbone and carbon branching, but does not include carbon atoms of the substituents, such as alkoxy substitutions and the like.

The terms "administer", "administering", or "administration", as used herein refer to either directly administering a compound or pharmaceutically acceptable salt of the compound or a composition to an animal, or administering a prodrug derivative or analog of the compound or pharmaceutically acceptable salt of the compound or composition to the animal, which can form an equivalent amount of the compound within the animal's body.

The term "subject" as used herein includes, without limitation, a human, mouse, rat, guinea pig, dog, cat, horse, cow, pig, monkey, chimpanzee, baboon, or rhesus monkey. In one embodiment, the animal is a mammal.

The term "conditions effective to" as used herein refers to synthetic reaction conditions that will be apparent to those skilled in the art of synthetic organic chemistry.

The term "effective amount" as used herein refers to an amount of a compound or pharmaceutically acceptable salt of a compound that, when administered to an animal, is effective to prevent, to at least partially ameliorate, or to cure, a condition from which the animal suffers or is suspected to suffer.

The term "pharmaceutically acceptable salt", as used herein, refers to salts derived from organic and inorganic acids of a compound described herein. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound described herein having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C$_1$-C$_6$)-alkylamine), such as N,N-dimethyl-N-(2-hydroxyethyl)amine or tri-(2-hydroxyethyl) amine; N-methyl-D-glucamine; morpholine; thiomorpholine; piperidine; pyrrolidine; and amino acids such as arginine, lysine, and the like. The term "pharmaceutically acceptable salt" also includes hydrates of a compound described herein.

The term "pharmaceutically acceptable carrier" as used herein refers to a diluent, adjuvant, excipient, or vehicle with which a heterodimeric probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the heterodimeric probes and pharmaceutically acceptable carriers preferably should be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "physiologically acceptable" as used herein refers to a composition that, in contact with a cell, isolated from a natural source or in culture, or a tissue of a host, has no toxic effect on the cell or tissue.

Compounds

The compounds described herein demonstrate reduced mineral affinity compared to many known bisphosphonate compounds currently used for treatment of osteoporosis and other bone disorders (e.g., minodronate, risedronate, alendronate, zoledronate, ibandronate). The presence of fluorine, chlorine, or hydrogen at the phosphonate-bearing carbon atom (i.e., R$_3$ in the compounds described herein) is believed to result in reduced mineral affinity. In known bisphosphonate compounds, this carbon atom bears an hydroxyl moiety which together with the two phosphonate moieties is thought to help create a high affinity for bone mineral. Previous studies demonstrated that, in other classes of bisphosphonates, such as pyridyl alkyl bisphosphonates and the gem phosphono-carboxylate analogs of bisphosphonates, replacement of the hydroxyl moiety with such moieties reduces the affinity for bone mineral and can reduce affinity for the FPPS enzymatic target site (e.g., halogen or hydrogen) and significantly lowers cellular potency. (Marma et al., *J. Med. Chem.*, 50: 5967-5975.)

The pyridylimidazoylalkyl bisphosphonate compounds described herein, however, demonstrate a high degree of cellular potency, despite the substitution at the carbon atom adjacent to the phosphonate groups, and the accompanying reduction in mineral affinity. This result is unexpected, as the reduction in mineral affinity is expected to lead to a marked reduction in in vivo potency. Moreover, the greater cellular potency (FPPS enzyme inhibition) provides a more potent antiresorptive effect in vivo than many previous bisphosphonate compounds.

The reduced mineral affinity of the bisphosphonate compounds described herein offers greater control of dosing, as the compound's effects on bone metabolism will dissipate faster than with traditional bisphosphonate compounds having higher mineral affinity. The reduced mineral affinity also provides faster release from bone and may offer greater utility to younger patients, patients of childbearing age, and for those that may require combination or sequential dosing of other bone therapeutic agents, particularly in comparison to known bisphosphonate compounds that are currently approved for use in treating bone disorders. It is believed that these lower mineral affinity properties may also offer more even distribution across the multiple bone types and sites in the skeleton. Alternatively, these features may provide improved effects at nearby cells that are less accessible by higher affinity analogs.

Faster release from the bone, subsequent to dosing, allows more flexible use of the bisphosphonate compounds described herein, compared to bisphosphonate compounds known in the art. For example, in some embodiments, the compound described herein can be used for defined periods of time that will allow discontinuation of therapy for contraindicative activities or subsequent use of alternative or additional drugs. For example, anabolic therapies that may be rendered less active when bone turnover is reduced. Similarly, the lower bone affinity offered by the compounds described herein results in less overall skeletal uptake, less overall reduction of bone turnover, and less effect on skeletal modeling/remodeling, thus leaving the regenerative processes of bone functioning more normally. This may result in a better quality of bone as more normal bone turnover is maintained while the typical anti-fracture benefits of bisphosphonate drugs are delivered. As a result, treatment is available to younger patients who might want to avoid the effects of traditional bisphosphonates (e.g., reduction in bone turnover and accompanying deleterious effects) over longer periods of time. Moreover, it is anticipated that the compounds described herein provide antiresorptive or fracture benefits while maintaining better bone quality, in contrast to high mineral affinity analogs that induce less physiological and extreme bone turnover reduction.

Other advantages of the low mineral affinity of the compounds described herein include a higher propensity for interacting deep within bone tissue and thus offering beneficial effects of bisphosphonates to osteocytes deep within the bone. In addition, lower mineral affinity compounds are more likely to produce higher concentrations in synovial fluid, as well as higher extracellular levels of bisphosphonate compound (e.g., around osteoclasts, macrophages, chondrocytes, and tumor cells), facilitating more effective daily, weekly or monthly administration. The compounds described herein exhibit lower total skeletal turnover reduction, as well as a more defined therapy as a result of faster release after ceasing therapy. This feature may therefore offer additional benefits during the treatment of multiple conditions associated with bone loss such as bone erosions associated with arthritic joints and tumor initiation and growth associated with bone metastasis.

In one embodiment, the bisphosphonate compounds described herein are administered as an adjuvant with one or more anti-inflammatory compounds. The use of higher affinity bisphosphonate compounds known in the art with anti-inflammatory compounds is limited due to toxicity issues related to the combination of these compounds. In particular, higher dosages of anti-inflammatory compounds are required to protect bone, when co-administered with known bisphosphonate compounds. Because of the higher dosages, however, side effects and other toxicity-related effects are quickly observed and the co-administration must be stopped. Because the compounds described herein have a lower affinity for bone, however, they can be used effectively to protect bone in combination with anti-inflammatory or immunomodulation agents at dosage levels that are low enough to not trigger toxic effects. Accordingly, the compounds described herein provide improved protection against bone erosion, while at the same time offering improved joint preservation, while inducing less overall skeletal turnover reduction than traditional bisphosphonates. In one embodiment, the compounds described herein are useful for inhibiting bone erosion. In another embodiment, the compounds described herein are useful for inhibiting both inflammation and bone erosion. For example, such anti-inflammatory, immunomodulatory and anti-erosion properties are achieved in some embodiments when the bisphosphonate compounds described herein are co-administered with an anti-inflammatory or immunomodulatory agent. In these embodiments, the anti-inflammatory or immunomodulatory agent can be administered at lower doses than it would be when administered on its own. Thus, in some embodiments, the bisphosphonate compound is administered in combination or in sequence with the one or more anti-inflammatory or immunomodulatory compounds. Exemplary anti-inflammatory or immunomodulatory compounds include, without limitation, biologic anti-inflammatory or immunomodulatory compounds such as tumor necrosis factor antagonists, NSAIDs, glococorticoids and methotrexate.

The synergy between the bisphosphonate compounds described herein is also beneficial for treatment of osteoarthritis. In osteoarthritis, the afflicted joints are known to exhibit higher bone turnover. Treatment with a combination of one or more of the bisphosphonate compounds described herein and an anti-inflammatory or immunomodulatory compound can normalize the turnover at these sites without producing excessive bone turnover in the remaining skeleton. In addition, the co-administration maximizes any potential anti-apoptotic effects on chondrocytes that are delivered to this joint by the virtue of these lower affinity bisphosphonate analogs. The compounds described herein are useful for improvement of joint function.

Similarly, the compounds described herein can also be co-administered with anabolic compounds. With bisphosphonate compounds known in the art, a wash out phase is necessary when treating patients who have been previously administered anabolic compounds, such as parathyroid hormone and prostaglandins. The lower bone affinity of the compounds described herein, however, results in less interference with these anabolic agents. Accordingly, the compounds described herein can be administered to patients treated with anabolic agents with little or no washout period. In one embodiment, the compounds described herein are co-administered with one or more anabolic compounds. One exemplary anabolic compound is a compound based on parathyroid hormones (PTH) such as PTH 1-34 (FORTEO®). Anabolic therapy is often prescribed to patients with very serious osteoporotic disease and/or those who do not respond to bisphosphonate therapy. Accordingly, the bisphosphonate compounds described herein are useful for treatment of osteoporotic disease, as well as subjects who respond poorly to bisphosphonate therapy.

Synthesis Procedures

The compounds and pharmaceutically acceptable salts described herein can be prepared using a variety of methods starting from commercially available compounds, known compounds, or compounds prepared by known methods. General synthetic routes to many of the compounds described herein are included in the following schemes. It is understood by those skilled in the art that protection and deprotection steps not shown in the Schemes may be required for these syntheses, and that the order of steps may be changed to accommodate functionality in the target molecule. The need for protection and deprotection, and the selection of appropriate protecting groups can be found, for example, in Greene and Wuts, *Protecting Groups in Organic Synthesis*, Second Edition, John Wiley & Sons (1991), which is incorporated by reference in its entirety.

In the schemes described herein, appropriate polar solvents include, but are not limited to, dimethyl sulfoxide, dimethylformamide, tetrahydrofuran, methanol and ethanol. Suitable acid binding agents include, but are not limited to, organic tertiary bases, such as, for example, triethylamine, triethanolamine, 1,8-diazabicyclo[5.4.0]undec-7-ene (DBU), and diisopropylethylamine (DIPEA); and alkaline metal carbonates, such as, for example, potassium carbonate and sodium carbonates. Suitable reducing agents include, but are not limited to, sodium cyanoborohydride and sodium triacetoxyborohydride.

Scheme 1, as shown in FIG. 1, illustrates one process for making compounds of Formula I, where $R_1$, $R_2$, and $R_3$ are as defined herein. As shown in Scheme 1, to prepare compounds of Formula I, the 5-azaindole compound 1 is reacted under conditions effective to produce compound 2, containing a leaving group at the 3-position of the 5-membered ring. Exemplary reagents include, without limitation, CuBr2. The reaction is carried out in an appropriate organic solvent, e.g., acetonitrile. Compound 2 is reacted under conditions effective to add a protecting group to the nitrogen of the 5-membered ring, resulting in formation of compound 3. Exemplary protecting groups include, without limitation, tert-butyloxycarbonyl boc). For example, in one embodiment, compound 2 is reacted with di-tert-butyl dicarbonate (i.e., $BOC_2O$). The reaction is carried out in appropriate solvents, such as DMAP and tetrahydrofuran. Compound 3 is reacted with vinyl phosphonate 3a under conditions effective to produce a mixture of isomers 4 and 5. For example, in some embodiments, the reaction is performed in the presence of n-butyl lithium at reduced temperature, e.g. −78° C. The reaction is carried out in appropriate solvents, e.g. tetrahydrofuran.

When $R_3$ is other than hydrogen (i.e., a halogen such as F or Cl), the mixture of compounds 4 and 5 is reacted with a halogenating compound, e.g., SLECTFLUOR® (Air Products, Inc.) under catalytic conditions, for example in the presence of an appropriate amount of a catalytic reagent, e.g., 18-crown-6, to produce a mixture of compounds 6 and 7. The reaction is carried out in appropriate solvents, e.g., potassium hydride and tetrahydrofuran at reduced temperature, e.g. 0° C.

Depending on the identity of $R_3$, the mixture of compound 4 and 5 (where $R_3$ is hydrogen) or the mixture of compounds 6 and 7 (where $R_3$ is other than hydrogen) is reacted under conditions effective to remove the protecting group. In one non-limiting embodiment, deprotection is carried out in the presence of TFA in acetonitrile and water. The desired 5-azaindole product, compound 6, is then isolated from the isomeric mixture by a suitable isolation/purification procedure, such as preparative HPLC. Compound 6 is then reacted under conditions effective to convert the ethoxy groups to hydroxy groups, thereby producing a compound of Formula I. In some embodiments, the reaction is carried out in the presence of trimethyl silylbromide.

The compounds and pharmaceutically acceptable salts of the compounds described herein are also useful in the manufacture of medicaments for treating or preventing disorder associated with abnormal calcium and phosphate metabolism in a mammal.

Pharmaceutical Compositions

Therapeutic compounds as described herein can be incorporated into pharmaceutical compositions. Such compositions typically include the active ingredient and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers can include, but are not limited to, physiological saline, bacteriostatic water, or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from pressured container or dispenser which contains a suitable propellant, e.g., a gas such as carbon dioxide, or a nebulizer. Such methods include those described in U.S. Pat. No. 6,468,798. Compositions for inhalation can also include propellants, surfactants, and other additives, e.g., to improve dispersion, flow, and bioavailability.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Pharmaceutically acceptable compositions of the present disclosure, therefore, may comprise a pharmaceutically-acceptable excipient. The term "pharmaceutically-acceptable excipient," as used herein, means any physiologically inert, pharmacologically inactive material known to one skilled in the art, which is compatible with the physical and chemical characteristics of the isomer herein. Pharmaceutically-acceptable excipients include, but are not limited to, polymers, resins, plasticizers, fillers, lubricants, diluents, binders, disintegrants, solvents, co-solvents, surfactants, preservatives, sweetening agents, flavoring agents, pharmaceutical-grade dyes or pigments, and viscosity agents.

Flavoring agents and dyes and pigments among those useful herein include those described in *Handbook of Pharmaceutical Excipients* ($4^{th}$ ed., Pharmaceutical Press 2003).

Suitable co-solvents include, but are not limited to, ethanol, isopropanol, and acetone.

Suitable surfactants include, but are not limited to, polyoxyethylene sorbitan fatty acid esters, polyoxyethylene monoalkyl ethers, sucrose monoesters, sodium lauryl sulfate, Tween 80®, and lanolin esters and ethers.

Suitable preservatives include, but are not limited to, phenol, alkyl esters of parahydroxybenzoic acid, benzoic acid and the salts thereof, boric acid and the salts thereof, sorbic acid and the salts thereof, chlorobutanol, benzyl alcohol, thimerosal, phenylmercuric acetate and nitrate, nitromersol, benzoalkonium chloride, cetylpyridinium chloride, methyl paraben, and propyl paraben.

Suitable fillers include, but are not limited to, starch, lactose, sucrose, maltodextrin, and microcrystalline cellulose.

Suitable plasticizers include, but are not limited to, triethyl citrate, polyethylene glycol, propylene glycol, dibutyl phthalate, castor oil, acetylated monoglycerides, and triacetin.

Suitable polymers include, but are not limited to, ethylcellulose, cellulose acetate trimellitate, hydroxypropylmethylcellulose phthalate, cellulose acetate phthalate, polyvinyl acetate phthalate.

Suitable lubricants include, but are not limited to, magnesium stearate, stearic acid, and talc.

The pharmaceutical compositions described herein, in some embodiments, optionally may comprise a chelating agent. The term "chelating agent," as used herein, means a molecule containing two or more electron donor atoms that can form coordinate bonds to a single metal ion. The term "chelating agent" is understood to include the chelating agent as well as salts thereof. For example, the term "chelating agent" includes citric acid as well as its salt forms.

The most common and widely used chelating agents coordinate to metal atoms through oxygen or nitrogen donor atoms, or both. Other less common chelating agents coordinate through sulfur in the form of —SH (thiol or mercapto) groups. After the first coordinate bond is formed, each successive donor atom that binds creates a ring containing the metal atom. A chelating agent may be bidentate, tridentate, tetradentate, etc., depending upon whether it contains two, three, four, or more donor atoms capable of binding to the metal atom. See *Kirk-Othmer Encyclopedia of Chemical Technology* ($4^{th}$ ed. 2001).

Chelating agents suitable for use in the compositions described herein include any pharmaceutically-acceptable chelating agent. Non-limiting examples of chelating agents suitable for use in the present disclosure include EDTA, citric acid, malic acid, tartaric acid, lactic acid, aspartic acid, glutamic acid, lysine, sodium hexametaphosphate, and combinations thereof.

A monodentate complexing agent may be used in place of a polydentate chelating agent. Suitable monodentate complexing agents include, but are not limited to, phosphates (e.g., sodium phosphate, sodium aluminum phosphate, sodium acid phosphate, dipotassium phosphate, disodium phosphate, monobasic) and carboxylic acids (e.g., fumaric acid, acetic acid). In one embodiment, the monodentate complexing agent is acetic acid.

The amount of chelating agent present in the oral dosage form of the present disclosure will depend on the particular chelating agent selected and the amount of bisphosphonate compound present in the oral dosage form. Generally, the oral dosage forms of the present disclosure will contain a safe and effective amount of a chelating agent suitable for achieving the desired chelating effect. In one embodiment, the oral dosage form contains from about 10 mg to about 1000 mg of a chelating agent per unit dose. In another embodiment, the oral dosage forms contain from about 10 mg to about 500 mg of a chelating agent per unit dose. When the chelating agent is EDTA, the preferred range is from about 10 mg to about 500 mg, preferably from about 25 mg to about 250 mg per unit dose. When the chelating agent is citric acid or any other chelating agent, the preferred range is from about 25 mg to about 1000 mg, preferably from about 50 mg to about 500 mg per unit dose.

Such pharmaceutical compositions are prepared, for example, using a method including admixing the compound or pharmaceutically acceptable salt of the compound and a pharmaceutically acceptable excipient. Admixing is accomplished using methods well known for admixing a compound or a pharmaceutically acceptable salt of a compound and a physiologically acceptable excipient. Examples of such excipients are well known to those skilled in the art and are prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), which is incorporated herein by reference in its entirety. Pharmaceutically acceptable excipients include are those that are compatible with the other ingredients in the formulation and biologically acceptable.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule.

The compounds or pharmaceutically acceptable salts of the compounds described herein may be administered orally or parenterally, neat or in combination with conventional pharmaceutical carriers as described above. The compounds or pharmaceutically acceptable salts of the compounds described herein can also be administered by any convenient route, for example, orally, by infusion or bolus injection, by absorption through epithelial or mucocutaneous linings (e.g., oral, rectal, vaginal, and intestinal mucosa, etc.) and can be administered together with another therapeutic agent.

It is understood that the dosage, regimen and mode of administration of these compounds will vary according to the malady and the individual being treated and will be subject to the judgment of the medical practitioner involved. In some embodiments, administration of one or more of the compounds or pharmaceutically acceptable salts of the compounds described herein begins at a low dose and is increased until the desired effects are achieved.

The amount of the compound or a pharmaceutically acceptable salt of the compound delivered is an amount that is effective for treating or preventing bone metabolism disorder. In addition, in vitro or in vivo assays are optionally be employed to help identify optimal dosage ranges. The precise dose to be employed will also depend on the route of administration, the condition, the seriousness of the condition being treated, as well as various physical factors related to the individual being treated, and should be decided according to the judgment of a health-care practitioner. The number and frequency of dosages corresponding to a completed course of therapy will be determined according to the judgment of a health-care practitioner.

The amount of the compound or a pharmaceutically acceptable salt of the compound that is effective for treating or preventing a bone disorder will typically range from about 0.01 mg/kg to about 1 g/kg of body weight per day, in one embodiment, from about 1 mg/kg to about 600 mg/kg body weight per day, in one embodiment, from about 1 mg/kg to about 250 mg/kg body weight per day, in another embodiment, from about 10 mg/kg to about 400 mg/kg body weight per day, in another embodiment, from about 10 mg/kg to about 200 mg/kg of body weight per day, in another embodiment, from about 10 mg/kg to about 100 mg/kg of body weight per day, in one embodiment, from about 10 mg/kg to about 25 mg/kg body weight per day, in another embodiment, from about 1 mg/kg to about 10 mg/kg body weight per day, in another embodiment, from about 0.001 mg/kg to about 100 mg/kg of body weight per day, in another embodiment, from about 0.001 mg/kg to about 10 mg/kg of body weight per day, and in another embodiment, from about 0.001 mg/kg to about 1 mg/kg of body weight per day.

A pharmaceutical composition according to the disclsoure can be in unit dosage form. In such form, the composition is sub-divided in unit dose containing appropriate quantities of the compound or pharmaceutically acceptable salt of the compound; the unit dosage form can be packaged compositions, for example, packeted powders, vials, ampoules, pre-filled syringes or sachets containing liquids. The unit dosage form can be, for example, a capsule or tablet itself, or it can be the appropriate number of any such compositions in package form. Such unit dosage form may contain from about 0.01 mg/kg to about 250 mg/kg, in one embodiment from about 1 mg/kg to about 250 mg/kg, in another embodiment from about 10 mg/kg to about 25 mg/kg, and may be given in a single dose or in two or more divided doses. Variations in the dosage will necessarily occur depending upon the species, weight and condition of the patient being treated and the patient's individual response to the medicament.

In one embodiment, the unit dosage form is about 0.01 to about 1000 mg. In another embodiment, the unit dosage form is about 0.01 to about 500 mg; in another embodiment, the unit dosage form is about 0.01 to about 250 mg; in another embodiment, the unit dosage form is about 0.01 to about 100 mg; in another embodiment, the unit dosage form is about 0.01 to about 50 mg; in another embodiment, the unit dosage form is about 0.01 to about 25 mg; in another embodiment, the unit dosage form is about 0.01 to about 10 mg; in another embodiment, the unit dosage form is about 0.01 to about 5 mg; and in another embodiment, the unit dosage form is about 0.01 to about 10 mg.

Any enteric coating which is insoluble at a pH below 5.5 (i.e., that generally found in the mouth, pharynx, esophagus, and stomach), but soluble at pH 5.5 or higher (i.e., that present in the small intestine and the large intestine) can be used in the practice of the present disclosure. Accordingly, when it is desired to effect delivery of the bisphosphonate and the chelating agent to the small intestine, any enteric coating is suitable which is wholly- or partially-insoluble at a pH below 5.5 and soluble at a pH 5.5 or above.

The enteric coating must be applied to the compressed tablet, the capsule (e.g., gelatin, starch, or hydroxypropylmethylcellulose) and/or the beads, particles or granules of active ingredient in a sufficient thickness so that the entire coating does not dissolve in gastrointestinal fluids at a pH below 5.5, but does dissolve at a pH of 5.5 or above. The dissolution or disintegration of the excipient coating generally does not occur until the entry of the coated dosage form into the small intestine.

It is expected that any anionic polymer exhibiting the requisite pH-dependent solubility profile can be used as an enteric coating in the practice of the present disclosure to achieve delivery of the bisphosphonate and chelating agent to the lower GI tract. The coating chosen must be compatible with the particular bisphosphonate active ingredient selected. The preferred polymers for use in the present disclosure are anionic carboxylic polymers. It is particularly preferred that the polymers are acrylic polymers, more preferably partly methyl-esterified methacrylic acid polymers, in which the ratio of free anionic carboxyl groups to ester groups is about 1:1.

The coating can, and usually will, contain a plasticizer and possibly other coating excipients such as coloring agents, surfactant, talc, and/or magnesium stearate, many of which are well known in the coating art. In particular, anionic carboxylic acrylic polymers usually will contain 10-25% by weight of a plasticizer, especially triethyl citrate, tributyl citrate, aceyltriethyl citrate, dibutyl phthalate, diethyl phthalate, polyethylene glycol, acetylated monoglycerides propylene glycol, and triacetin. Conventional coating techniques such as fluid-bed or pan coating are employed to apply the coating. Coating thickness must be sufficient to ensure that the oral dosage form remains essentially intact until the desired site of delivery in the lower GI tract is reached.

The solid oral dosage form may be in the form of a coated compressed tablet which contains particles or granules of the bisphosphonate active ingredient and the chelating agent, or of a soft or hard capsule (e.g., gelatin, starch, or hydroxypropylmethylcellulose), coated or uncoated, which contains beads or particles of the bisphosphonate active ingredient and the chelating agent, which themselves are enterically coated.

For sustained release of the bisphosphonate and chelating agent a sustained release polymer is required to control the dissolution rate of the bisphosphonate and chelating agent from the dosage form. If the bisphosphonate and chelating agent are both soluble (defined as 33 mg/ml or greater in water) then high levels of sustained release polymers are required. Sustained release polymers include but are not limited to hydroxypropylmethylcellulose, hydroxypropylcellulose and Carbomer.

Methods of Use

The present disclosure further relates to a method of treating, preventing or ameliorating disorders of bone metabolism, such as those characterized by abnormal calcium and phosphate metabolism. These methods include the step of administering to a human or other mammal in need thereof a safe and effective amount of a pharmaceutical composition delivered to said human or other mammal via the oral dosage forms described herein.

Diseases characterized by abnormal calcium and phosphate metabolism include, but are not limited to, osteoporosis, secondary osteoporosis, secondary osteoporosis stemming from osteoporosis, osteoarthritis, Paget's disease (osteitis deformans), hyperparathyroidism, hypercalcemia of malignancy, osteolytic bone metastasis, myositis ossificans progressiva, calcinosis universalis, and such afflictions as arthritis, neuritis, bursitis, tendonitis, bone pain, and other inflammatory conditions which predispose involved tissue to loss or deposition of calcium phosphates. The compounds described herein are also useful for other bone disorders and conditions such as, without limitation, fracture repair, prosthesis integration, and osteonecrosis (e.g., of hip or knee). The compounds described herein are also useful for the prevention and treatment of skeletal related events associated with cancer such as metastasis, tumor growth, bone pain, fractures, and such afflictions as arthritis (including bone disease and joint function in osteoarthritis). Further, the compounds described herein are also useful for treatment and prevention of additional skeletal related events induced during the treatment of cancer, such as hormone ablation therapy, aromatase inhibitor therapy, and androgen ablation therapy, particularly in patients suffering from breast or prostate cancer.

The compounds described herein are also useful for the prevention and treatment of parasitic disorders such as malaria and Chagas disease, and disorders of the gastrointestinal tract such as intestinal parasites, and irritable bowel disease. In some embodiments, the compounds described herein are, in some embodiments, useful to inhibit or treat parasitic infections, such as protozoan infections and diseases including malaria, leishmaniasis, trypanasomal diseases, entamoeba, giardia, and cryptosporidial infections.

In some embodiments, the compounds described herein are useful for treating or preventing inflammation disorders. Such disorders include, without limitation, rheumatoid arthritis, and irritable bowel disease. In some embodiments, when used for treating or preventing inflammation disorders, the compounds described herein may be used in combination with one or more anti-inflammatory compounds.

In some embodiments, the compounds described herein are useful for treating, preventing or ameliorating dental disorders. Exemplary disorders include, without limitation, cavities and periodontal disease. In some embodiments, the compounds described herein are useful for treatment related to dental surgical procedures, such as tooth implantation.

In some embodiments, the compounds described herein are useful for treatment related to orthopedic joint implants, for example to improve fixation of artificial joints, or to prevent loosening of implanted joints. In further embodiments, the compounds described herein have orthopedic uses, such as to promote or facilitate fracture repair and bone regeneration, either when used as a sole therapy on in conjunction with other pharmaceutical or non-pharmaceutical orthopedic therapy.

In further embodiments, the compounds described herein offer orthopedic utility in the outcomes of hip, knees or other skeletal sites in both pediatric and adult populations.

The oral dosage forms described herein are suitable for administration to pediatric or adult patients in need of such treatment.

In some embodiments, the compounds described herein are useful as part of hormone ablation therapy, for example, in patients suffering from breast cancer or prostate cancer. In some embodiments, the compounds described herein are useful as part of aromatase inhibitor therapy, for example in patients suffering from cancer. In some embodiments, the compounds described herein are useful as part of androgen ablation therapy, for example in patients suffering from prostate cancer or other diseases.

The oral dosage forms of the present disclosure are suitable for administration to a patient according to a continuous dosing interval of daily, weekly, three times per month, twice monthly, and monthly.

When administered for the treatment or inhibition of a particular disease state or disorder, it is understood that the effective dosage may vary depending upon the particular compound or pharmaceutically acceptable salt of the compound utilized, the mode of administration, the condition, and severity thereof, of the condition being treated, as well as the various physical factors related to the individual being treated. In therapeutic application, the compounds and pharmaceutically acceptable salts of the compounds described herein are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

The compounds and pharmaceutically acceptable salts of the compounds described herein are also useful in the manufacture of medicaments for treating a bone metabolism disorder in a mammal. Similarly, the compounds and pharmaceutically acceptable salts of the compounds described herein are also useful in the manufacture of medicaments for treating a bone metabolism disorder.

One aspect of the present disclosure, therefore, encompasses compounds, or pharmaceutically acceptable salts thereof, where the compound has a structure according to Formula I

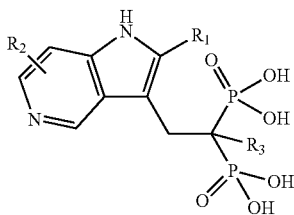

(I)

where $R_1$ is hydrogen, hydroxyl, lower alkyl, methoxy, or F; $R_2$ is hydrogen, hydroxyl, lower alkyl, or F; and $R_3$ is hydrogen or a halogen.

In embodiments of this aspect of the disclosure, $R_1$ and $R_2$ can be each independently hydrogen, hydroxyl, methyl, ethyl, t-butyl, or F.

In some embodiments of the disclosure, $R_1$ can be hydrogen or a lower alkyl, and $R_2$ can be hydrogen, hydroxyl, methyl, or F.

In other embodiments of this aspect of the disclosure, $R_1$ can be hydrogen, ethyl, or t-butyl, and $R_2$ can be hydrogen, hydroxyl, methyl, or F. In some embodiments, $R_3$ can be hydrogen or F.

In some embodiments of this aspect of the disclosure, $R_1$ can be hydrogen, $R_2$ can be hydrogen or methyl, and $R_3$ can be hydrogen or F.

In some other embodiments of this aspect of the disclosure, $R_1$ is ethyl or t-butyl, $R_2$ is hydrogen, and $R_3$ is hydrogen or F.

Embodiments of this aspect of the disclosure can be, but are not limited to, compounds wherein the compound has a structure according to Formula Ia:

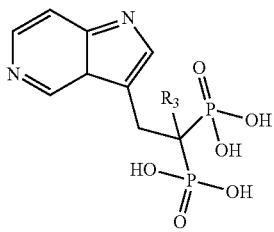

(Ia)

In one embodiment, thereof, $R_3$ is hydrogen and the compound is 5-azaindol-3-yl-ethyl-bisphosphonic acid. In another embodiment thereof, $R_3$ is F and the compound is 1-fluoro-(5-azaindol)-3-yl-ethyl-bisphosphonic acid.

Another aspect of the disclosure encompasses pharmaceutical compositions that comprise a compound, or a pharmaceutically acceptable salt thereof, wherein the compound has a structure according to formula I

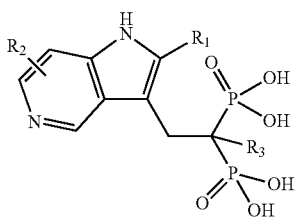

(I)

where $R_1$ is hydrogen, hydroxyl, lower alkyl, methoxy, or F; $R_2$ is hydrogen, hydroxyl, lower alkyl, or F; and $R_3$ is F, Cl, or hydrogen, and a pharmaceutically acceptable carrier.

In embodiments of this aspect of the disclosure, $R_1$ and $R_2$ can be each independently hydrogen, hydroxyl, methyl, ethyl, t-butyl, or F.

In some embodiments of the disclosure, $R_1$ can be hydrogen or a lower alkyl, and $R_2$ can be hydrogen, hydroxyl, methyl, or F.

In other embodiments of this aspect of the disclosure, $R_1$ can be hydrogen, ethyl, or t-butyl, and $R_2$ can be hydrogen, hydroxyl, methyl, or F. In some embodiments, $R_3$ can be hydrogen or F.

In some embodiments of this aspect of the disclosure, $R_1$ can be hydrogen, $R_2$ can be hydrogen or methyl, and $R_3$ can be hydrogen or F.

In some other embodiments of this aspect of the disclosure, $R_1$ is ethyl or t-butyl, $R_2$ is hydrogen, and $R_3$ is hydrogen or F.

In some embodiments of this aspect of the disclosure, the compound can have a structure according to Formula Ia:

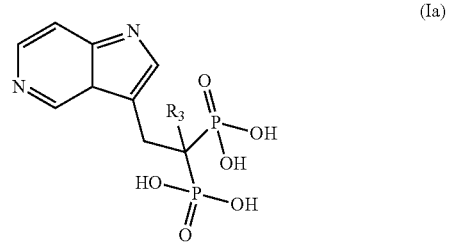

(Ia)

In one of these embodiments $R_3$ can be hydrogen and the compound is 5-azaindol-3-yl-ethyl-bisphosphonic acid. In another embodiment, $R_3$ is F and the compound is 1-fluoro-(5-azaindol)-3-yl-ethyl-bisphosphonic acid.

In other embodiments of this aspect of the disclosure, the composition can further comprise at least one pharmaceutically active ingredient other than a bisphosphonic acid, or pharmaceutically acceptable salt thereof. In these embodiments, the at least one pharmaceutically active ingredient can be selected from the group consisting of, but is not limited to, an anti-inflammatory, an immunomodulator, a chelator, a musculoskeletal anabolic agent, and a combination thereof.

Yet another aspect of the disclosure encompasses methods of modulating calcium or phosphate metabolism in a subject animal or human, the method comprising administering to the subject animal or human an effective amount of a compound, or pharmaceutically acceptable salt thereof, where the compound has a structure according to Formula I

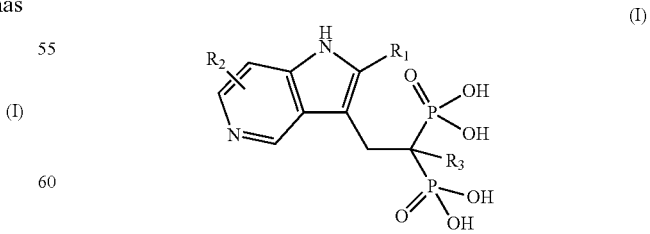

(I)

where $R_1$ is hydrogen, hydroxyl, lower alkyl, methoxy, or F; $R_2$ is hydrogen, hydroxyl, lower alkyl, or F; and $R_3$ is F, Cl, or hydrogen, whereupon the calcium or phosphate metabolism in the subject animal or human is modified.

In embodiments of the methods of this aspect of the disclosure, the calcium or phosphate metabolism in the subject animal or human before administering the compound thereto can be abnormal and associated with a skeletal disorder. In some embodiments of this aspect of the disclosure, the skeletal disorder can be selected from the group consisting of, but not limited to, osteoporosis, rheumatoid arthritis, osteoarthritis, Paget's disease, alveolar bone loss, a bone-related cancer, and an orthopedic disorder.

In other embodiments, the disorder may be a non-skeletal disorder such as, but not limited to, a non-bone cancer, an inflammatory or immunomodulatory disorder, and a parasitic disorder. In these embodiments, the parasitic disorder can be, but is not limited to, malaria, leishmaniasis, a trypanasomal disease, an entamoebal infection, a giardia infection, and a cryptosporidial infection.

In the embodiments of the methods of this aspect of the disclosure, the compound administered to the subject animal or human can modify the activity of farnesyl pyrophosphate synthase in the subject animal or human.

In the embodiments of the methods of this aspect of the disclosure, the compound, or pharmaceutically acceptable salt thereof, or is 5-azaindol-3-yl-ethyl-bisphosphonic acid or 1-fluoro-(5-azaindol)-3-yl-ethyl-bisphosphonic acid.

It should be noted that ratios, concentrations, amounts, and other numerical data may be expressed herein in a range format. It is to be understood that such a range format is used for convenience and brevity, and thus should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9% or ±10%, or more of the numerical value(s) being modified.

The following examples illustrate the production of representative compounds described herein.

EXAMPLES

Example 1

3-bromo-5-azaindole

Referring now to the Scheme 1 as shown in FIG. 1, a solution of 3.0128 g (25.51 mmol) of 5-azaindole (Atlantic SciTech Group) in 50 mL of acetonitrile was placed in a 250 mL three-neck round-bottom flask equipped with a magnetic stirrer, thermocouple, nitrogen bleed, and cooling ice bath. A total of 17.10 g (76.53 mmol, 3 eq.) of solid CuBr2 was added portion-wise to the flask at 17° C. in 10 min. The resulting green suspension was stirred at room temperature until no starting material was observed by TLC (approximately 1-2 hours, Rf=0.23 for 5-azaindole and 0.49 for 3-bromo-5-azaindole in EtOAc/MeOH=9:1). The reaction mixture was cooled to 10° C. and then was slowly quenched by addition of 7N ammonia in methanol solution (110 mL). The resulting blue solution was concentrated on rotavap at room temperature, and the residue was extracted with ethyl acetate (3×80 mL). The organic extract was dried over $Na_2SO_4$, filtered, and concentrated to residual volume of about 50 mL. The temperature of the residue was brought to reflux resulting in the dissolving of all solids, and then hexane was added to the hot mixture until crystallization occurred. The resulting suspension was cooled on an ice bath, the product was filtered, washed with cold EtOAc/hexane=1:3 and then hexane, and dried. The 3-bromo-5-azaindole was an off-white solid, yield 3.52 g (70% yield).

Example 2

N-BOC-3-bromo-5-azaindole

Referring now to the Scheme 1 as shown in FIG. 1, a solution of 3.5601 g (18.06 mmol) of 3-bromo-5-azaindole (2) and 0.4651 g (3.8 mmol, 21 mol %) of dimethylaminopyridine (DMAP) in 80 mL of THF was placed in a 250 mL three-neck round-bottom flask equipped with a magnetic stirrer, thermocouple, nitrogen bleed, and cooling ice bath. A total of 4.7769 g (21.88 mmol, 1.2 eq.) of BOC2O was added to the flask at 17° C., and the resulting mixture was stirred until starting 3-bromo-5-azaindole disappeared, as monitored by TLC (generally, overnight stirring at room temperature). The resulting yellow solution was concentrated on rotavap, washed with 100 mL of saturated sodium bicarbonate, and extracted with dichloromethane (3×80 mL). The organic phase was dried over $Na_2SO_4$ and concentrated on rotavap to afford 6.57 g of orange solid. This crude material was purified on CombiFlash using hexane/ethyl acetate as eluent to give 5.25 g (97% yield) of n-boc-3-bromo-5-azaindole (3) as a white solid.

Example 3

Tetraethyl-5-azaindol-3-yl-ethyl-bisphosphonate

Referring now to the Scheme 1 as shown in FIG. 1, a solution of 2.9138 g (9.805 mmol) of N-boc-3-bromo-5-azaindole in 50 mL of anhydrous THF was placed in a 250 mL three-neck round-bottom flask equipped with a magnetic stirrer, thermocouple, nitrogen bleed, and cooling dry ice/acetone bath. A total of 4.3 mL (10.75 mmol, 1.1 eq.) of 2.5N solution of n-butyl lithium in hexane was slowly added to N-boc-3-bromo-5-azaindole with the rate to maintain the reaction temperature below −73° C. The resulting orange-colored solution stirred at −73° C. for 30 min, and a total of 2.9485 g (9.82 mmol, 1 eq.) of vinyl bisphosphonate, tetraethyl ethane-1,1-bisphosphonate (prepared according to the procedures given in *J. Org. Chem.* 1986, 51, 3488-3490, incorporated herein by reference in its entirety) was slowly added and after stirring at −73° C. for 20 min the resulting mixture was allowed to warm to room temperature. The reaction was quenched with 100 mL of cold water, and the products extracted with ethyl acetate (3×50 mL).

The organic phase was dried over $Na_2SO_4$ and then concentrated on rotavap to give 5.67 g of red oil. This crude material was purified on CombiFlash using ethyl acetate/methanol as eluent to give 3.6 g (71% yield) of a mixture (80:20 by NMR) of two isomers, tetraethyl-n-boc-(5-azaindol-3-yl)-ethyl-bisphosphonate and tetraethyl-n-boc-(5-azaindol-2-yl)-ethyl-bisphosphonate. The isomers were inseparable by chromatography failed due to close $R_f$-values ($R_f$=0.17 in EtOAc/MeOH=9:1).

To achieve acceptable separation, the obtained mixture of isomers (3.6 g) was stirred for two days with 5 mL of TFA in a mixture of 50 mL of acetonitrile containing 0.1% TFA and 20 mL of water containing 0.1% TFA (mobile phases for HPLC). After two days complete deprotection was observed by HPLC. The volume of the reaction mixture was decreased to 50 mL by concentration on rotavap, and the clear solution was purified by preparative HPLC (four runs) to separate the azaindol-2-yl from the azaindol 3-yl. The purity of the obtained fractions was monitored by $^{31}P$ NMR. The pure fractions were combined, concentrated on rotavap, and the obtained clear oil was washed with 50 mL of saturated sodium bicarbonate. The organic material was extracted with dichloromethane (3×30 mL), and the combined organic phases were dried over sodium sulfate and concentrated on rotavap to afford 1.14 g (39% yield) of tetraethyl-5-azaindol-3-yl-ethyl-bisphosphonate as a white solid.

Example 4

5-azaindol-3-yl-ethyl-bisphosphonic acid

Referring now to the Scheme 1 as shown in FIG. 1, a solution of tetraethyl-n-boc-(5-azaindol-3-yl)-ethyl-bisphosphonate (0.54 g, 1.29 mmol) in 15 mL of anhydrous chloroform was placed in a 25 mL 3-neck round bottom flask equipped with a magnetic stirrer, thermocouple, condenser, heating mantle, and nitrogen bleed. Neat TMSBr (1.75 g, 11.43 mmol, about 9 eq.) was added to this solution at room temperature, and the resulting solution stirred at 50° C. until only the mass M−1=305 was observed in LC-MS in negative mode (about 22 hours). The reaction mixture was cooled to room temperature and concentrated on rotavap, diluted with 10 mL of anhydrous dichloromethane, and filtered via a 0.45 m Teflon membrane filter.

Referring now to the Scheme 1 as shown in FIG. 1, a total of 4 mL of water was slowly added to the solution, and the precipitated white solid was filtered and consequently washed with water (3×5 mL), methanol (2×5 mL), and ether (2×15 mL), and then dried under high vacuum at 40° C. until constant weight. (5-Azaindol-3-yl)-ethyl-bisphosphonic acid (146 mg, 37% isolated yield) was obtained as a white solid. Elemental analysis (%) calculated for $C_9H_{12}N_2O_6P_2 \cdot 0.2H_2O$ (309.75): C, 34.90; H, 4.03; N, 9.04. Found C, 34.81; H, 3.78; N, 8.83.

$^1H$ NMR (400 MHz, $D_2O+KOD$, ppm): 2.27 (m, 1H, J=21.6 Hz, 6 Hz), 3.29 (m, 2H, J=15.2 Hz, 6.4 Hz), 7.36 (s, 1H), 7.41 (d, 1H, J=6 Hz), 8.10 (d, 1H, J=6 Hz), 8.96 (s, 1H).

$^{13}C$ NMR APT (100 MHz, $D_2O+KOD$, ppm): 22.06 (s, up), 40.97 (t, J=113 Hz, down), 107.14 (s, down), 116.7 (d, J=8 Hz, up), 124.31 (s, up), 124.72 (s, down), 138.77 (s, down), 140.06 (s, up), 141.66 (s, down).

$^{31}P$ NMR (162 MHz, $D_2O+KOD$, ppm): 19.82 (s)

Example 5

HAP Affinity

Mineral affinity for hydroxyapatite was evaluated by chromatographic profiling of the novel bisphosphonate compounds. Hydroxyapatite (HAP) ceramic spheres (20 µm diameter, BioRad) were packed in a 0.66×6.5 cm glass column (Omnifit®). The HAP columns were attached to a Waters 650E Advanced Protein Purification System (FPLC) (Millipore) in a running buffer of 1 mM KPO3 at pH 6.8. Each compound was prepared in 1 mM KPO3 buffer at pH 6.8 and 400 µmoles were injected into the FPLC system. The bisphosphonate compounds were eluted in a gradient of phosphate buffer, concentration increasing from 1 mM up to 1000 mM and detected by a Waters 484 UV absorbance detector (Millipore) at their optimum wavelength. Table 1 shows the HAP retention profiles of each compound (determined in triplicate for statistical analyses). Longer retention times (minutes) correspond with higher affinity to the HAP sphere and, correspondingly, higher mineral affinity.

TABLE 1

HAP Affinity

| Example | Retention time (min) |
|---|---|
| 5-Azaindol-3-yl)-ethyl-bisphosphonic acid | 6.3 |
| Minodronate | 10.33 |
| Risedronate | 9.97 |
| Alendronate | 17.5 |
| Zoledronate | 12.53 |

Example 6

FPPS Inhibition

The compounds were evaluated for in vitro inhibition of human farnesyl pyrophosphate synthase (FPPS), the major molecular target of nitrogen-containing bisphosphonate compounds. Inhibition of FPPS correlates with inhibition of bone resorption in vivo. Accordingly, FPPS inhibition is an indicator of the potency of the bisphosphonate compounds. This method is disclosed in Dunford J. E., et al., *J. Med. Chem.*, 51, 2187-2195 (2008) and Dunford, J. E., et al., *J Pharmacol Exp Ther.*, 296, 235-242 (2001), the disclosures of which are incorporated herein by reference. Recombinant human FPPS was expressed and purified as described in Dunford J. E., et al., *J. Med. Chem.*, 51, 2187-2195 (2008). For kinetic analysis, 40 ng (1 pmol) of pure FPP synthase were assayed in a final volume of 100 µL buffer containing 50 mM Tris pH 7.7, 2 mM MgCl2, 0.5 mM TCEP and 20 µg/mL BSA.

The concentrations of substrates, GPP and IPP (14C-IPP, 400 KBq/µmol) were 10 µM each in the standard reaction. Reactions also contained the appropriate concentration of the appropriate bisphosphonate compound. Reactions were started with the addition of enzyme at 2 µg/mL in enzyme dilution buffer (10 mM HEPES pH 7.5, 500 Mm NaCl, 5% glycerol, 2 mM TCEP, 20 µg/mL BSA) and allowed to proceed for an appropriate period of time at 37° C. The reaction mixtures were then extracted with 0.4 mL of ligroin to separate reaction products from unused substrate and, after thorough mixing, 0.2 mL of the ligroin upper phase was combined with 4 mL of general purpose scintillant. The final inhibition constant ($K_i$) and $IC_{50}$ value, shown in Table 2, were calculated as described in the literature.

These data demonstrate the enzyme inhibitory activity of the bisphosphonate compounds described herein is consistent with the inhibitory activity of known effective bisphosphonate compounds, despite the reduced affinity for bone mineral shown in Example 5, above.

TABLE 2

FPPS inhibition

| Example | $IC_{50}$ nM[1] | $K_i$ |
|---|---|---|
| 5-Azaindol-3-y1)-ethyl-bisphosphonic acid | 6.6 | 0.6 |
| Minodronate | 1.9 | 0.0005 |
| Risedronate | 5.7 | 0.36 |
| Alendronate | 330.4 | 57 |

[1]After pre-incubation

Example 7

In Vivo Analysis

In vivo tests can also be performed to demonstrate the properties of the compounds of the invention. Such models include the Schenk Model to evaluate in vivo bone resorption inhibition and mineralization inhibition in an animal model system. The general principles of this model system are disclosed in Shinoda et al., *Calcif. Tissue Int.* 35: 87-99 (1983); and in Schenk et al., *Calcif. Tissue Res.* 11: 196-214 (1973), the disclosures of which are incorporated herein by reference in their entireties. The collagen induced arthritis (CIA) rat model is an in vivo model that provides for an evaluation of the inhibition of inflammation as well as inhibition of bone erosion. The method is described at Bendele et al. *Arthritis & Rheumatism*, 43: 2648-2659 (2000), incorporated herein by reference in its entirety. Finally, evaluation for in vivo bone resorption inhibition potency by an animal model system known can be performed via the thyroparathyroidectomized (TPTX) rat model. The general principles of this model system are disclosed in Russell et al. *Calcif. Tissue Res.* 6: 183-196 (1970), and in Muhlbauer & Fleisch, *Mineral Electrolyte Metab.*, 5, 296-303 (1981). The disclosures of these references are incorporated herein by reference in their entireties.

We claim:

1. A compound, or a pharmaceutically acceptable salt thereof, wherein the compound has a structure according to Formula I

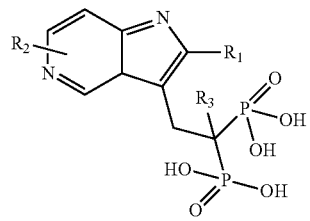
(I)

wherein:
$R_1$ is hydrogen, hydroxyl, lower alkyl, methoxy, or F;
$R_2$ is hydrogen, hydroxyl, lower alkyl, or F; and
$R_3$ is hydrogen or a halogen.

2. The compound of claim 1, wherein $R_1$ and $R_2$ are each independently hydrogen, hydroxyl, methyl, ethyl, t-butyl, or F.

3. The compound of claim 1, wherein $R_1$ is hydrogen or a lower alkyl, and $R_2$ is hydrogen, hydroxyl, methyl, or F.

4. The compound of claim 1, wherein $R_1$ is hydrogen, ethyl, or t-butyl, and $R_2$ is hydrogen, hydroxyl, methyl, or F.

5. The compound of claim 1, wherein $R_3$ is hydrogen or F.

6. The compound of claim 1, wherein $R_1$ is hydrogen, $R_2$ is hydrogen or methyl, and $R_3$ is hydrogen or F.

7. The compound of claim 1, wherein $R_1$ is ethyl or t-butyl, $R_2$ is hydrogen, and $R_3$ is hydrogen or F.

8. The compound of claim 1, wherein the compound has a structure according to Formula Ia:

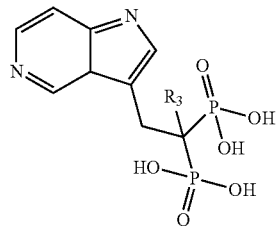
(Ia)

wherein $R_3$ is hydrogen and the compound is 5-azaindol-3-yl-ethyl-bisphosphonic acid, or $R_3$ is F and the compound is 1-fluoro-(5-azaindol)-3-yl-ethyl-bisphosphonic acid.

9. A pharmaceutical composition comprising:
a compound, or a pharmaceutically acceptable salt thereof, wherein the compound has a structure according to Formula I

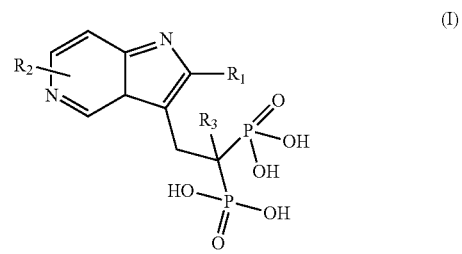
(I)

wherein:
$R_1$ is hydrogen, hydroxyl, lower alkyl, methoxy, or F;
$R_2$ is hydrogen, hydroxyl, lower alkyl, or F; and
$R_3$ is F, Cl, or hydrogen; and
a pharmaceutically acceptable carrier.

10. The composition of claim 9, wherein $R_1$ and $R_2$ are each independently hydrogen, hydroxyl, methyl, ethyl, t-butyl, or F.

11. The composition of claim 9, wherein $R_3$ is hydrogen or F.

12. The composition of claim 9, wherein $R_1$ is hydrogen; $R_2$ is hydrogen or methyl; and $R_3$ is hydrogen or F.

13. The composition of claim 9, wherein $R_1$ is ethyl or t-butyl; $R_2$ is hydrogen; and $R_3$ is hydrogen or F.

14. The composition of claim 9, wherein the compound has a structure according to Formula Ia:

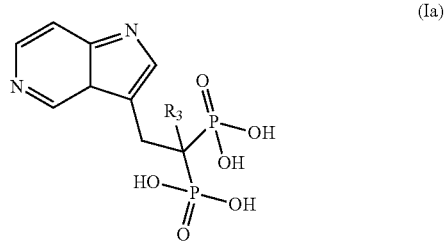
(Ia)

wherein $R_3$ is hydrogen and the compound is 5-azaindol-3-yl-ethyl-bisphosphonic acid, or $R_3$ is F and the compound is 1-fluoro-(5-azaindol)-3-yl-ethyl-bisphosphonic acid.

15. The composition of claim 9, wherein the compound further comprises at least one pharmaceutically active ingredient other than a bisphosphonic acid, or pharmaceutically acceptable salt thereof.

16. The composition of claim 15, wherein the at least one pharmaceutically active ingredient is selected from the group consisting of: an anti-inflammatory, an immunomodulator, a chelator, a musculoskeletal anabolic agent, and a combination thereof.

* * * * *